(12) United States Patent
Kriger (10) Patent No.: US 10,017,078 B2
(45) Date of Patent: Jul. 10, 2018

(54) RELOCATABLE/REPLACEABLE PAD FOR ACCURATE VEHICLE OCCUPANT WEIGHT MEASUREMENT

(71) Applicant: Yefim G Kriger, Ansonia, CT (US)

(72) Inventor: Yefim G Kriger, Ansonia, CT (US)

( * ) Notice: Subject to any disclaimer, the term of this patent is extended or adjusted under 35 U.S.C. 154(b) by 0 days.

(21) Appl. No.: 15/787,576

(22) Filed: Oct. 18, 2017

(65) Prior Publication Data

US 2018/0043795 A1 Feb. 15, 2018

Related U.S. Application Data

(60) Continuation-in-part of application No. 15/430,219, filed on Feb. 10, 2017, which is a division of application No. 14/282,715, filed on May 20, 2014, now Pat. No. 9,566,877.

(60) Provisional application No. 62/496,539, filed on Oct. 21, 2016, provisional application No. 61/956,059, filed on May 30, 2013.

(51) Int. Cl.
| | |
|---|---|
| *G01G 19/12* | (2006.01) |
| *G01G 19/414* | (2006.01) |
| *G01G 19/44* | (2006.01) |
| *B60R 21/015* | (2006.01) |
| *B60N 2/02* | (2006.01) |
| *A61B 5/00* | (2006.01) |
| *B60N 2/00* | (2006.01) |

(52) U.S. Cl.
CPC ........ *B60N 2/002* (2013.01); *B60R 21/01512* (2014.10); *G01G 19/4142* (2013.01); *A61B 5/6893* (2013.01)

(58) Field of Classification Search
CPC ............. B60N 2/002; B60R 21/01512; G01G 19/4142; A61B 5/6893
See application file for complete search history.

(56) References Cited

U.S. PATENT DOCUMENTS 5,573,269 A * 11/1996 Gentry ............... G01G 19/4142
177/144
5,804,887 A * 9/1998 Holzapfel ............. B60N 2/002
180/282

(Continued)

OTHER PUBLICATIONS

Lu Cheng et al., "Design of a Capacitive Flexible Weighing Sensor for Vehicle WIM System", Sensors No. 7, pp. 1530-1544, 2007.

(Continued)

*Primary Examiner* — Randy Gibson
(74) *Attorney, Agent, or Firm* — Anatoly Frenkel (57) ABSTRACT

The specification and drawings present a new apparatus and method for providing an accurate and convenient weighing of a vehicle occupant using a relocatable/replaceable multi-purpose on-board vehicle occupant weighing (REMBOW) methodology including a REMBOW pad mounted on a REMBOW seat frame in a vehicle to improve safe engagement of an air bag as well as raising and monitoring possible health related issues of the vehicle occupant(s). The occupant weighing can be performed, using, as a non-limiting example, a kemoder elimination of a separate occupant's feet weighing (KEF) technology, where kemoder is a key element for moderating of an accuracy and convenience of an occupant weighing (i.e., a weighing moderator) and for starting a measuring process.

20 Claims, 6 Drawing Sheets

(56) References Cited

U.S. PATENT DOCUMENTS

| | | | | |
|---|---|---|---|---|
| 5,865,463 | A * | 2/1999 | Gagnon | G01G 19/4142 280/730.2 |
| 5,942,695 | A * | 8/1999 | Verma | G01G 19/4142 177/144 |
| 5,991,676 | A * | 11/1999 | Podoloff | G01G 19/4142 177/144 |
| 6,039,344 | A * | 3/2000 | Mehney | B60N 2/002 177/144 |
| 6,279,981 | B1 * | 8/2001 | Mesnage | B60N 2/002 296/65.03 |
| 6,345,839 | B1 * | 2/2002 | Kuboki | B60N 2/002 280/735 |
| 6,378,900 | B1 * | 4/2002 | Stanley | B60N 2/002 280/735 |
| 6,578,917 | B1 * | 6/2003 | Aubert | B60N 2/002 297/317 |
| 6,649,848 | B2 * | 11/2003 | Kriger | G01G 19/4146 128/921 |
| 6,784,379 | B2 * | 8/2004 | Breed | B60N 2/002 177/144 |
| 6,816,807 | B2 | 11/2004 | Kriger | |
| 6,929,324 | B2 * | 8/2005 | Enomoto | B60N 2/002 177/144 |
| 6,956,465 | B2 * | 10/2005 | Meyer | G01G 17/06 180/272 |
| 6,992,562 | B2 * | 1/2006 | Fuks | B60N 2/002 340/5.52 |
| 7,059,446 | B2 * | 6/2006 | Murphy | B60N 2/002 177/144 |
| 7,134,715 | B1 * | 11/2006 | Fristedt | B60N 2/002 297/180.12 |
| 7,137,665 | B2 * | 11/2006 | Osawa | B60N 2/071 297/344.1 |
| 7,289,035 | B2 * | 10/2007 | Nathan | B60N 2/002 280/268 |
| 7,434,481 | B2 * | 10/2008 | Hawes | B60N 2/002 177/136 |
| 7,465,272 | B2 * | 12/2008 | Kriger | G01G 19/4142 128/921 |
| 7,808,394 | B2 * | 10/2010 | Nathan | B60N 2/3002 280/268 |
| 7,991,530 | B2 | 8/2011 | Cho et al. | |
| 8,010,255 | B2 * | 8/2011 | Darraba | B60N 2/002 342/30 |
| 9,140,588 | B2 | 9/2015 | Endo et al. | |
| 9,156,384 | B2 | 10/2015 | Takayasu et al. | |
| 2005/0150705 | A1 * | 7/2005 | Vincent | B60N 2/002 180/271 |
| 2008/0136227 | A1 * | 6/2008 | Lim | B60N 2/002 297/217.3 |
| 2008/0294370 | A1 | 11/2008 | Kruger | |
| 2017/0267197 | A1 | 9/2017 | Kriger | |

OTHER PUBLICATIONS

Tsutomu Takano, "Development of Occupant Classification System", Nissan Motor Co., Ltd, Japan, Paper 206, Proceedings—18th International Technical Conference on the Enhanced Safety of Vehicles, Nagoya, Japan, May 19-22, 2003.

Occupant Crash Protection, Section 571.208, Standard No. 208, Title 49 "Transportation", Federal Motor Vehicle Safety Standard, Oct. 1, 2011.

* cited by examiner

RELOCATABLE/REPLACEABLE PAD FOR ACCURATE VEHICLE OCCUPANT WEIGHT MEASUREMENT

CROSS-REFERENCE TO RELATED APPLICATIONS

This application claims the benefit of the filing date under 35 USC 119(e) of U.S. Provisional Application No. 62/496,539 filed on Oct. 21, 2016, the contents of which are incorporated herein by reference thereto. Moreover, this application is a continuation-in-part claiming the benefit of pending U.S. patent application Ser. No. 15/430,219 filed on Feb. 10, 2017, which is a divisional patent application of U.S. patent application Ser. No. 14/282,715 filed on May 20, 2014 now U.S. Pat. No. 9,566,877 which is issued on Feb. 14, 2017 and claims priority to U.S. Provisional Application No. 61/956,059 filed on May 30, 2013, the contents each of which are incorporated herein in their entirety by reference thereto.

TECHNICAL FIELD

The invention generally relates to weighing technology. More particularly but not exclusively, this invention relates to using a relocatable/replaceable pad for accurate vehicle occupant weight measurement (e.g., based on KEF technology) to improve safety of a vehicle occupant as well as possibly raising and monitoring health related issues of the vehicle occupant(s).

BACKGROUND OF THE INVENTION

There are at least two important problems related to the safety and health of the vehicle occupants. One of these problems, the problem of vehicle occupant safety, has now become a nation-wide problem for the USA and other countries. Most American cars are equipped with a safety air bag system such as Supplemental Restraint Systems (SRS).

To improve performance of various safety devices such as SRS, operations of the safety devices have been controlled in accordance with the weight of a passenger sitting on a vehicle seat.

In some safety air bag SRS systems, a vehicle Passenger Classification System is described that uses the differences in weight between adults and small children, and a control unit identifies vehicle occupants using input values from weight sensors installed between the leg frames fixed on the floor and moving rails of a car seat.

In other SRS systems, the sensors for measuring the weight of a seated passenger are disposed between moving rails of a car seat and a frame of the vehicle seat.

In the U.S. Pat. No. 7,991,530 "System and method for classifying vehicle occupant" by Cho et al., a vehicle Occupant Classification System is described that uses the differences in weight between adults and small children, and a control unit identifies vehicle occupants using input values from weight sensors installed between the leg frames and moving rails of a seat, and results of sensing are transmitted to an Airbag Control Unit (ACU). However, the above-described system for classifying a vehicle occupant has problems in that it is difficult to install sensors in a seat and the complexity of work increases because respective components of the system have to be individually installed in a seat.

Because a load sensor is typically disposed in a narrow space between the vehicle floor and the vehicle seat, it is difficult to do maintenance on the load sensor. Further, dismounting the entire vehicle seat for easier maintenance is inefficient.

In another type of safety air bag the SRS system described in the U.S. Pat. No. 9,140,588, "Vehicle seat comprising load sensor and side frame with upper-side protruding section and lower-side protruding section" by Endo et al., a vehicle passenger's weight measurement device for a vehicle seat comprises a movable rail on a fixed rail, a load sensor which is mounted on an upper surface of the movable rail, a cushion frame which is mounted on the load sensor, and a pan frame, wherein the efficiency of the load sensor maintenance is improved. However, there is a dimension error or an assembling position error when the passenger's weight measurement device is assembled, when the vehicle seat is fixed to the passenger's weight measurement device or when the passenger's weight measurement device is fixed to the vehicle floor, or the like. Accordingly, it has been difficult to assemble the passenger's weight measurement device.

In this regard, another type of conventional safety air bag system is described in the U.S. Pat. No. 9,156,384, "Vehicle seat comprising load sensor and side frame having a concave part", by Takayasu et al., to provide a passenger's weight measurement device for a vehicle seat, which is more easily assembled, and to provide an attachment structure for a load sensor. In this invention, a vehicle seat includes a load sensor that is configured to measure a load applied from an occupant and that has an extending rod, a seat cushion frame that includes right and left side frames that extend along a front-rear axis, and a bracket member attaching the load sensor to at least one of the right and left side frames.

As we can see from the inventions described above, the occupant's weight measuring sensor has been moved from the low part of the sliding rails, where it touches the upper part of the lower rails fixed on the vehicle's floor. This is a useful step in improving of the access, maintenance, and life span of the weight sensor relative to the structure of the air bag devices where the weight sensors are installed on the leg frames fixed on the floor.

Despite these improvements, the Passenger Classification System of the air bag SRS systems is still limited because the capacity of the load sensor is fixed and the weight span of the possible vehicle occupants is too wide for accurate weight measurements in different weight categories.

SUMMARY OF THE INVENTION

According to a first aspect of the invention, a relocatable/replaceable multi-purpose on-board vehicle occupant weighing (REMBOW) pad for occupant weighing in a vehicle comprising: a lower frame detachably mounted on a sliding portion of a REMBOW seat frame; a weighing unit having corresponding components and optimized for a predefined weighting range, configured to provide a weight signal indicative of a weight of an occupant of the vehicle sitting on the REMBOW pad for generating a measured weight signal indicative of a measured weight of the occupant in order to secure a safe use of a corresponding air bag; and an upper frame comprising a seat cushion to cover parts of the REMBOW pad.

According further to the first aspect of the invention, the occupant weighing may be performed using a kemoder elimination of a separate occupant's feet weighing (KEF) technology, where the kemoder is a key element for moderating (a weighing moderator) of accuracy and convenience of weighing and for generating a starting signal for measuring process.

According further to the first aspect of the invention, the REMBOW pad may further comprise a transceiver for providing communications, using wireless or wired connection, between the REMBOW pad and components/devices outside of the REMBOW pad in the vehicle or outside the vehicle.

According still further to the first aspect of the invention, the lower frame of the REMBOW pad may be detachably mounted on side frames that are fixed on sliding rails of the REMBOW seat frame.

Still further according to the first aspect of the invention, the weighing unit may be located in the lower frame of the REMBOW pad.

According further to the first aspect of the invention, the vehicle may be a car, a motor vehicle, or a self-driving car.

According yet further still to the first aspect of the invention, the REMBOW pad of claim 1, may further comprise a controller/processor with a memory, for managing and coordinating performance of the weighing unit. Further, the controller/processor may be configured to identify the occupant of the vehicle and a corresponding record, using a fingerprint identifier.

Yet still further according to the first aspect of the invention, the controller/processor may be configured to start recording weight measurements performed by the weighing unit in response to a corresponding starting signal for measuring process from a kemoder, where the kemoder is a weighing moderator and a key element for moderating of accuracy and convenience of weighing and for generating the starting signal for the measuring process. Further, the weighing moderator may comprise an audio command module configured to provide the corresponding starting signal activated by a voice of the occupant of the vehicle.

According further still to the first aspect of the invention, the REMBOW pad may comprise a processing electronic module, for providing to the controller/processor, when the starting signal is received by the controller/processor, the processed weight signal which is indicative of the weight in predefined units of the occupant of the vehicle sitting on the REMBOW pad, the processed weight signal can be generated in response to the weight signal indicative of the weight of the occupant from the weighing unit, so that the controller/processor can be further configured, in response to the processed weight signal, to provide the measured weight signal indicative of a measured weight of the occupant to any of a) a vehicle safety system to adjust a force of the corresponding air bag in action, b) a health indication and preventive system in the vehicle and c) a health indication and prevention system outside the vehicle.

Still yet further according to the first aspect of the invention, the controller/processor may be configured to provide a warning signal that the measured weight of the occupant exceeds the predefined weighting range of the weighing unit and that it may be necessary to substitute for an appropriate RENBOW pad with a larger weighing capacity. Still further, the REMBOW pad can be detachably mounted on the REMBOW seat frame of a driver of the vehicle, so that when the measured weight is in a predetermined range, the REMBOW pad can disable an ignition system of the vehicle.

According yet further still to the first aspect of the invention, the controller/processor may be configured to estimate a clothes weight of the occupant based at least on a geographical location of the vehicle, atmospheric temperature and a current date, and to subtract the estimated clothes weight from the measured weight of the occupant to determine a health-related weight of the occupant, and further configured to provide the health-related weight of the occupant to one or more of a) a health indication and preventive system in the vehicle and b) a health indication and preventive system outside the vehicle. Further, the health indication and preventive system can be configured to manage one or more of: a pre-fitness program, a fitness program, an obesity prevention program and a kidney disease prevention program.

According still yet further to the first aspect of the invention, the weighing unit may comprise strain gages that are fixed on the lower frame of the REMBOW pad, and then the upper frame of the REMBOW pad may be fixed on the rods of the strain gages.

According yet further still to the first aspect of the invention, the weight signal may be generated without a seat belt being fastened, so that the measured weight signal indicative of the measured weight of the occupant directly corresponds to the weight signal.

According further still to the first aspect of the invention, the weight signal is generated with a seat belt being fastened, so that the measured weight signal indicative of the measured weight of the occupant without the seat belt being fastened may be extrapolated using a statistically derived coefficient between weight measurements with or without seat belt being fastened, using a Weight Error from the Belt Elimination (WEBEL) method.

According to a second aspect of the invention, a non-transitory computer readable storage medium tangibly storing computer program instructions capable of being executed by a computer processor, the computer program instructions defining code for: receiving a starting signal for recording weigh measurements of an occupant in a vehicle sitting on a relocatable/replaceable multi-purpose on-board vehicle occupant weighing (REMBOW) pad having a lower frame detachably mounted on a sliding portion of a REMBOW seat frame, where the REMBOW pad comprises a weighing unit having corresponding components and optimized for a predefined weighting range, and configured to provide a weight signal indicative of a weight of an occupant of the vehicle sitting on the REMBOW pad; receiving, in response to the starting signal, a processed weight signal, in predefined units, of the occupant of the vehicle sitting on the REMBOW pad from a processing electronic module of the REMBOW pad which is responsive to the weight signal indicative of the weight of the occupant from the weighing unit; and providing, based on the received the processed weight signal, a measured weight signal indicative of a measured weight of the occupant of the vehicle to a vehicle safety system in order to secure a safe use of a corresponding air bag.

According to a third aspect of the invention, a relocatable multi-purpose on-board vehicle occupant weighing (REMBOW) system comprising: a REMBOW seat frame comprising a sliding portion, a relocatable/replaceable multi-purpose on-board vehicle occupant weighing (REMBOW) pad for occupant weighing in a vehicle, the REMBOW pad comprising: a lower frame detachably mounted on the sliding portion of a REMBOW seat frame; a weighing unit having corresponding components and optimized for a predefined weighting range, configured to provide a signal indicative of a weight of an occupant of the vehicle sitting on the REMBOW pad for generating a measured weight signal indicative of a measured weight of the occupant of the vehicle; and an upper frame comprising a seat cushion to cover parts of the REMBOW pad; and the REMBOW system further comprising a vehicular control system configured to secure a safe use of a corresponding air bag based on the measured weight signal.

BRIEF DESCRIPTION OF THE DRAWINGS

These and other features and aspects of the present disclosure will become better understood when the following detailed description is read, with reference to the accompanying drawings, in which like characters represent like parts throughout the drawings, wherein.

DETAILED DESCRIPTION

New apparatus and method are presented for providing an accurate and convenient weighing of a vehicle occupant using a relocatable/replaceable multi-purpose on-board vehicle occupant weighing (REMBOW) methodology including a REMBOW pad mounted on a REMBOW seat frame in a vehicle to improve safe engagement of an air bag as well as raising and monitoring possible health related issues of the vehicle occupant(s). The occupant weighing can be performed, using, as a non-limiting example, a kemoder elimination of a separate occupant's feet weighing (KEF) technology, where kemoder is a key element for moderating of an accuracy and convenience of an occupant weighing (i.e., a weighing moderator) for starting a measuring process as further discussed herein.

Using the KEF technology can be an important tool to provide effectiveness and required accuracy of the REMBOW methodology. It is based on a horwest (horizontal weighing stability) effect that states: the value of a weight measurement of an object located in a closed system on a weighing unit doesn't change while this object provides a bi-directional force in a horizontal direction of a predetermined value to a vertical surface of another object, which is a predetermined distance away. The horwest effect can be used to implement the simplified weighing apparatus for vehicle occupant weighing. An existence of the horwest effect is easy to demonstrate by the following experiment.

Put any human body weighing scale (a postal electrical scale or a mechanical scale with continual weight measurements could be the best) against the wall. Step onto the scale and check your weight. Touch a wall very gently by an arm pressing the wall in a horizontal direction. If you push the wall in a horizontal direction with a force of about 10 to 30 pounds, the display of the postal electrical scale or mechanical scale with the continual weight measurements will show approximately the same value of your weight that you measured before pushing the wall. If you use any digital human body floor weighing scale, make several measurements and find out your average body weight. Before making an experiment with the wall, calibrate the scale. Before stepping onto the scale, push the wall very gently by your hand in a horizontal direction, and step onto the scale. The scale display will show approximately the same value of your weight if you push the wall in a horizontal direction with a force up to 10 to 30 lb.

As the horwest effect description states, an object located on a weighing platform does not change the value of its weight measurement if the force provided by this object is applied in a horizontal direction to a vertical surface of another object. If the force is not applied horizontally, a vertical component of an applied force will influence the weight measurement of the object and will corrupt the weight measurement of the object on the weighing platform.

Let us make a few of definitions:

1. Hocpoint (a point of a vehicle compressed or stretched in a horizontal direction) is a sensitive point or area of a vertical piece of a vehicle which, according to the horwest effect, does not change the occupant's weight measurement if the vehicle occupant compresses or stretches it in a horizontal direction, and this activity according to the third Newton's law produces a force that provides an occupant support to conveniently lift up and keep out from the floor his/her feet during the weight measurement. There are at least several convenient hocpoints in a vehicle.

2. The simplest on-board vehicle weighing apparatus may be designed by utilizing only one weighing unit connected to the car seat of the vehicle occupant and pushing feet to a vertical surface of above mentioned piece of the vehicle in a horizontal direction because pushing feet to a vertical surface of another object in a horizontal direction will conveniently secure them on another object and will not influence the weight measurement of the vehicle occupant according to the horwest effect. Theoretically, it is possible to design such simplified weighing apparatus to accurately weigh the vehicle occupant and just simply push his/her feet horizontally against a substance such as a passive flat vehicle vertical piece. But to employ such weighing apparatus to accurately weigh the vehicle occupant and just push his/her feet against a substance such as a passive flat vehicle vertical surface in a strongly horizontal direction is impractical because the vehicle occupant is not able to push the feet against any vehicle surface during the measurement in the exactly horizontal direction. The problem may be solved by designing and employing a part that secures the vehicle occupant's pushing feet and redirects a feet pushing force in the horizontal direction. This part can be a weighing moderator and is a Key Element that Moderates two problems: a vehicle occupant's feet securing and controlling the feet force in a horizontal direction. This weighing moderator is called a kemoder.

A basic kemoder is a point or area that includes at least one hocpoint compressed or stretched by a vehicle occupant in a horizontal direction. A more advanced kemoder can provide a horizontal redirection for the force created by the vehicle occupant while compressing or stretching a spring or any elastic substance, such as a rubber, included in the kemoder.

3. A low level weighing moderator (LLK kemoder) is the kemoder that may be pressed by a low part of the vehicle occupant's body (foot or leg).

4. A high level weighing moderator (HLK kemoder) is the kemoder that may be pressed (dragged) by an upper part of the vehicle occupant's body (finger, palm, nape of the head, or elbow) and can be located above the occupant's waist.

According to one embodiment, a convenient Kemoder Elimination of a separate occupant's Feet weighing (KEF) technology can be provided that will enable application of a simplified weighing apparatus based on the horwest effect and employ only one weighing unit.

Figure 1:
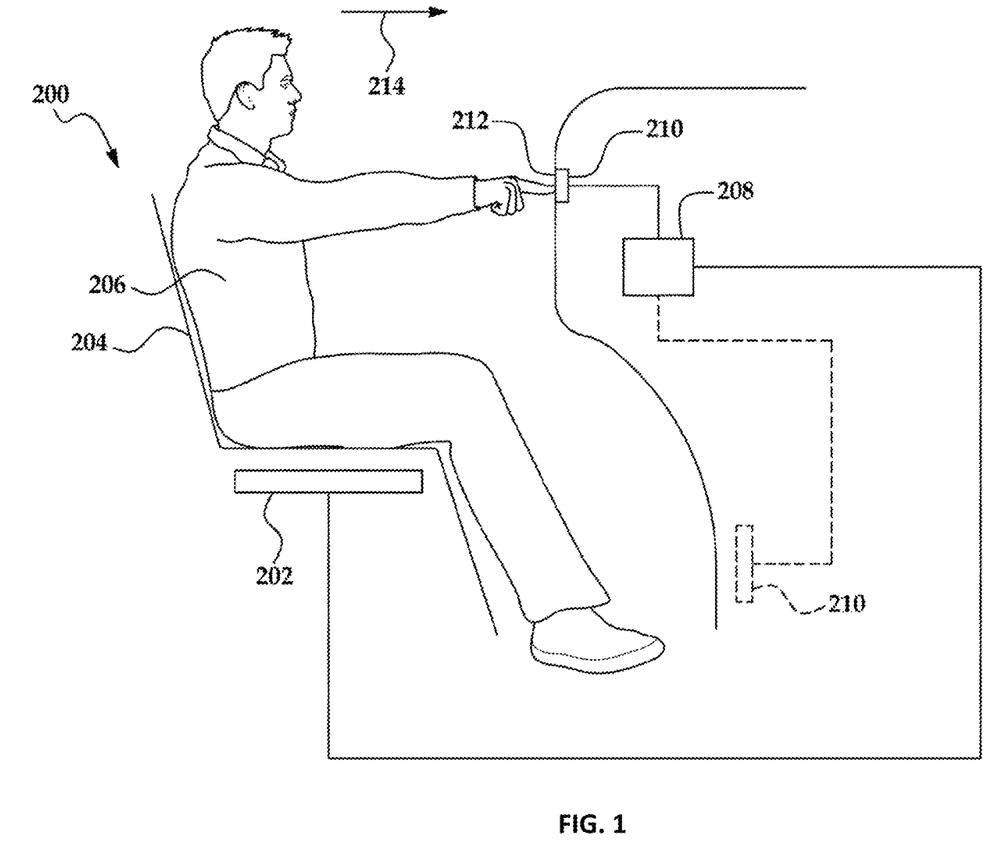
FIG. 1 is a non-limiting exemplary diagram of an on-board occupant weighing system demonstrating application of the KEF technology, according to an embodiment of the invention.

Moreover, the innovative KEF technology can provide a simplified and accurate occupant's weight measurement in a car or a motor vehicle, especially a passenger vehicle such as an automobile, a van, a self-driving car, a corporate vehicle, a limousine, or a truck equipped with an occupant safety device such as air bag Supplemental Restraint System (SRS) by employing a weighing unit (weight sensors) connected to the seat of the vehicle occupant, whose output is connected to the computing and control unit of the SRS, by pushing horizontally a switch of the weighing moderator, located above the waist of the occupant on a substantially vertical surface of the vehicle (for example, on a steering wheel, an instrument panel, or a dash board) at the beginning of the trip, and simultaneously, conveniently lifting feet above the floor and keeping them up during the weight measurement, measuring occupant's weight by the weighing unit (see FIG. 1 and a corresponding description). Subsequent processing of the collected weight of the vehicle's occupant by the computing and control unit while receiving the signal from the switch of the weighing moderator, modifying this original weight measurement of the vehicle occupant by the current values of the morphological data and factors of the car trip situation and transmitting this processed value of the vehicle occupant's weight to the air bag control unit to apply, in case of a collision, an appropriate force to the occupant's body, whose value will be calculated according to the modified and accurately measured occupant's original weight. The accuracy of weighing a vehicle's occupant and, accordingly, providing an accurate value of the force applied to the different weights of the occupants' bodies may be improved up to 20-30% by employing KEF technology.

It is further noted that the priority documents of the current invention, namely pending U.S. patent application Ser. No. 15/430,219 filed on Feb. 10, 2017, U.S. Pat. No. 9,566,877 issued on Feb. 14, 2017 and U.S. Provisional Application No. 61/956,059 filed on May 30, 2013, can provide a more detailed description of the novel horwest effect and KEF technology.

The main components for using the REMBOW methodology/system can be identified as the REMBOW pad mounted on the REMBOW seat frame. According to an embodiment of the invention, the REMBOW pad for occupant weighing in a vehicle can comprise: a weighing unit having corresponding components and optimized for a predefined weighting range, configured to provide a weight signal indicative of a weight of an occupant of the vehicle sitting on the REMBOW pad for generating a measured weight signal indicative of a measured weight of the occupant in order to secure a safe use of a corresponding air bag; and an upper frame of the REMBOW pad comprising a seat cushion to cover parts of the REMBOW pad.

Moreover, the weighting unit can have different weight capacity ranges and modifications, and can be located in the lower frame of the REMBOW pad (like in a non-limiting example in FIG. 2), in the upper frame of the REMBOW pad or be shared in both. The REMBOW seat frame is typically a fixed part in the car. The REMBOW pad, containing the corresponding weighing unit with the predefined weighting range, is a relocatable/replaceable part of the system and may be easily reinstalled multiple times in different cars or motor vehicles, such as a passenger vehicle, an automobile, a van, a self-driving car, a corporate vehicle or a bus, a limousine, a tourist bus, a truck, a boat, and the like. Once installed for a driver or a passenger, the REMBOW pad may provide accurate weighing of the drivers or passengers having substantially different weight categories by only substituting for the REMBOW pad having a different/desired weight capacity/range of the weighing unit and, for example, employing the accurate, simplified and secure occupant weighing KEF technology based on the weighing moderator (kemoder).

Thus, according to an embodiment of the invention, the REMBOW methodology can provide the simplified and secure weight measurements of a driver and passengers of a vehicle (e.g., members of one of family).

In a further embodiment, the REMBOW pad may comprise a controller/processor with a memory located in the lower/upper frame, for managing and coordinating performance of the weighing unit. The functionality of the controller/processor may depend on a scope of its functionalities which is further discussed in reference to FIGS. 2-6.

For example, the controller/processor may be configured to identify the occupant of the vehicle and a corresponding record, using a fingerprint identifier. This embodiment can be used with an accurate weighing unit that is located in the REMBOW pad of the back seat passenger and can employ a weighing moderator (kemoder) conveniently located on the seatback of the vehicle occupant sitting in front of the back seat passenger, and the weighing moderator can include a fingerprint sensor, whose sensing (touching) surface is located vertically.

In another embodiment, the controller/processor may be configured to start recording weight measurements performed by the weighing unit in response to a corresponding starting signal for measuring process from a kemoder, e.g., when a vehicle occupant (a driver or a passenger) pushes in horizontal direction a weighing moderator/kemoder (e.g., located above the waist of the occupant) and simultaneously lifting feet above the floor. In this case the kemoder can act as a switch providing a corresponding starting signal for recording weight measurements to the controller/processor of the REMBOW pad. Moreover, the weighing moderator/kemoder can comprise an audio command module configured to provide the aforementioned starting signal for recording weight measurements using activation by a voice of the occupant of the vehicle at the same time the occupant pushing horizontally the kemoder and lifting feet above the floor.

In a further embodiment, the REMBOW pad can further comprise a processing electronic module, configured to provide to the controller/processor, after the starting signal is received by the controller/processor from the kemoder (weighing moderator), the processed weight signal which is indicative of the weight in predefined units of the occupant of the vehicle sitting on the REMBOW pad, the processed weight signal is generated in response to the weight signal indicative of the weight of the occupant from the weighing unit. Then, the controller/processor is further configured, in response to the processed weight signal, to provide the measured weight signal indicative of a measured weight of the occupant to any of a) a vehicle safety system to adjust a force of the corresponding air bag in action, b) a health indication and preventive system in the vehicle and c) a health indication and prevention system outside the vehicle.

Yet in another embodiment, the REMBOW pad of a driver seat, when the processed weight of a driver/occupant is within a predetermined range, the REMBOW pad is configured to disable an ignition system of the vehicle. This embodiment can protect a small child trying to drive a vehicle.

This embodiment may be implemented using a unit of Prohibition of Driving by the Children (PDC), e.g., a special application program stored in a memory and executed by the controller/processor of the REMBOW pad shown in FIG. 2, as described below. This applications program can suppress the ignition of the vehicle if the operator/driver/occupant on the driver's seat will have a weight in a range from $W_{min}$ to $W_C$. The predefined value of $W_c$ for the REMBOW system can be, for example, 25.6 kg. This level of the $W_C$ can be chosen, for example, to satisfy a maximum value for the 6-years old children provided in a paper Number 206, by Tsutomu Takano, Nissan Motor Co., LTD, Japan. It was shown in this paper that according to regulations of *FMVSS*208 (*Federal Motor Vehicle Safety Standard No. 208*), the maximum weight of the child AC06 (children of 6-years old) is 25.6 kilograms. The lower level $W_{min}$ can be a predefined weight which can be chosen arbitrarily based on a minimum possible weight (i.e., sensitivity) measured by the weighing unit with a predefined accuracy. For example, $W_{min}$ can be chosen to be about 5 kilograms (or 10 pounds).

Furthermore, to eliminate a possible accidental suppression of the ignition when the occupant moves his/her body on the car seat, a timer can be used to delay suppressing the ignition if the weight measured by the weighing unit does not hold between $W_{min}$ and $W_C$ for a predefined time interval $T_C$.

According to a further embodiment, the controller/processor can be configured to estimate a clothes weight of the occupant based at least on one or more of a geographical location of the vehicle (e.g., determined by a vehicle GPS), atmospheric temperature and a current date (i.e. a time of the year), and to subtract the estimated clothes weight from the processed weight of the occupant to determine a health-related weight of the occupant. Then the REMBOW pad may be configured (e.g., using a wired and/or wireless transmission) to provide a health-related signal indicative of the health-related weight of the occupant to one or more of a) a health indication and preventive system in the vehicle and b) a health indication and prevention system outside the vehicle.

It is noted that normally the weight signals indicative of the weight of the occupant can be generated without a seat belt being fastened, so that the measured weight signal indicative of the measured weight of the occupant directly corresponds to the weight signal. However, according yet to another embodiment, measuring the weight of an occupant of the vehicle using REMBOW methodology (e.g., using KEF technology) described herein may be performed with or without a seat belt being fastened, resulting in a small difference/error between these two measurements.

According to an embodiment of the invention, for improving an accuracy of weighing an occupant by using the REMBOW/KEF technology and eliminating a small error that may happen from the attached seat belt in a vehicle, a method of Weight Error from the Belt Elimination (WEBEL) can be employed. The WEBEL method can provide measuring the weight of the occupant twice: 1) when the seat belt is not fastened, and 2) when the seat belt is fastened, and a seat belt signal from a corresponding switch being provided to the controller/processor for informing that the seat belt is fastened.

Then, the difference between these two occupant's body weight measurements can provide an error of the seat belt fastening influence, and after collecting enough statistical data, can be used to weigh an occupant when the seat belt is fastened. Thus the WEBEL method can be used for weighing the driver in a vehicle when the seat belt is fastened, so that the measured weight without the seat belt being fastened can be extrapolated using a statistically derived coefficient.

Figure 2:
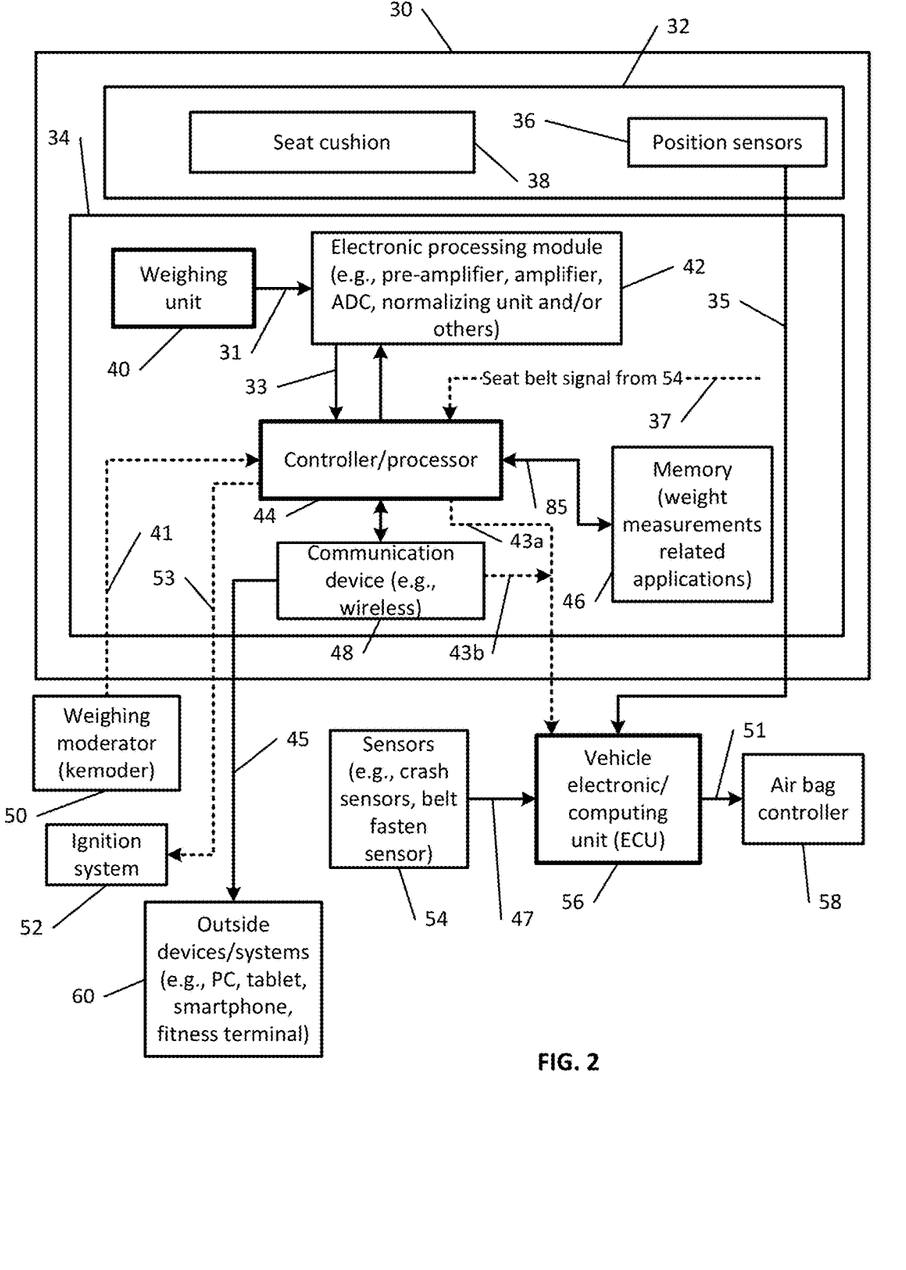
FIG. 2 is a block-diagram of a REMBOW pad, according to an embodiment of the invention.

According to one embodiment, the REMBOW pad can further comprise a transceiver for providing communications, using a wireless or wired connection, between the REMBOW pad and components/devices outside of the REMBOW pad in the vehicle or outside the vehicle (more details are provided in reference to FIG. 2).

According to a further embodiment, the weighing unit can comprise strain gages that are fixed on the lower frame of the REMBOW pad, where the upper frame of the REMBOW pad can be fixed on the rods of the strain gages. Moreover, the lower frame can be detachably mounted on a side frames that are fixed on sliding rails of the REMBOW seat frame (details are provided in reference to FIGS. 4 and 5). Further, the weighing unit, in general, may utilize different technologies such as load cells with strain gages, capacitive elements, and the like.

FIGS. 1-6 demonstrate non-limiting examples of various embodiments of the invention. It is noted that identical or similar parts/elements are designated using the same reference numbers in different figures.

FIG. 1 is an exemplary non-limiting diagram of an on-board occupant weighing system 200 in accordance with an embodiment of the invention demonstrating application of the KEF technology.

In one embodiment, the system 200 may be located in a vehicle. The system 200 includes a weighing unit 202 operatively connected to a seat 204 of a vehicle. The weighing unit 202 is configured to provide an output indicative of a weight of an occupant's 206 when he is seated on the seat 204. The system further may comprise a computing and control unit 208 operatively coupled to the weighing unit 202 and at least one switch 210 operatively coupled to the computing and control unit 208 (equivalent to a controller/processor 44 in FIG. 2). The switch 210 is behind a vertical surface 212 of the vehicle proximate to the seat 204, wherein the switch 210 is configured to provide an output when a force is applied to the surface 212 of the vehicle proximate to the switch 210 in the horizontal direction of arrow 214, wherein the computing and control 208 unit only processes the output from the weighing unit 202 when the output of the switch 210 is received by the computing and control unit 208.

In an alternative embodiment, the switch 210 may be located proximate to an occupant's feet so the force in the direction of arrow 214 can be applied by the feet. Alternatively the switch 210 may be located proximate to the occupant's hand and the force is applied by the hand/finger in the direction of arrow 214. Still further and in yet another embodiment, there may be two switches one proximate to the feet and one proximate to the hands, and the force in the direction of arrow 214 may be applied in by either the hand(s) or the feet or foot or both the hand(s) and the feet or foot. As stated herein, in any scenario, the feet of the occupant should be raised from a vehicle floor during weight measurement using KEF technology.

FIG. 2 is a block-diagram of a REMBOW pad 30, according to an embodiment of the invention. FIG. 2 is a simplified block diagram that is suitable for practicing the exemplary embodiments of this invention, and a specific manner in which components of the REMBOW pad 30 operate. The REMBOW pad 30 comprises a lower frame 34 and an upper frame 32. The lower frame 34 of the REMBOW pad 30 comprises a weighing unit 40, electronic processing module 42, a controller/processor 44, a memory 46, and a communication device 48 (e.g., wireless).

The upper frame 32 of the REMBOW pad 30 comprises a seat cushion 38 to cover parts of the REMBOW pad 30 and positioning sensors 36. The seat cushion 38 can be made to provide a desired shape and an angle of elevation to provide the anti-submarining features of the REMBOW pad 30. The lower frame 34 of the REMBOW pad 30 can provide secure and detachable mounting of the REMBOW pad 30 on a sliding portion of the upper surface of the REMBOW seat frame 10 (e.g., shown in FIGS. 4a and 4b) using side frames, sliding rails or a pan frame of the REMBOW seat frame 10. Various fasteners, screws, clips, cylindrical or tapered pins, bars and the like can be used to secure the mounted REMBOW pad 30. Thus, when the REMBOW system is installed in a vehicle, the lower surface of the lower frame 34 of the REMBOW pad 30 can be promptly and easily detachably attached to an upper surface 21 of side frames 20 or to sliding rails 14 (or to a pan frame if used) of the REMBOW seat frame 10 (e.g., see examples in reference to FIGS. 4a, 4b, 5a and 5b).

In one non-limiting example, the weighing unit 40 in FIG. 2 may comprise load cell sensors (e.g., four) that are fixed on the lower frame 34 of the REMBOW pad 30. The weight of the occupant seated on the cushion 38 of the REMBOW pad 30 is applied to the lower frame 34 through the upper frame 32 of the REMBOW pad 30 that can be fixed on the rods of the load cell sensors that in turn can be fixed on the lower frame 34 of the REMBOW pad 30. The load cell sensors can convert the weight of the occupant into an electric signal 31 (a weight signal indicative of the weight of the occupant).

Moreover, the load cell sensors can be fixed by bolts on the upper surface of the lower frame 34 of the REMBOW pad 30 through the corresponding openings in the lower frame 34 of the REMBOW pad 30 and can be arranged so as to be apexes of a square or a rectangle. There can be openings in the upper surface of a rectangular pan frame (if used) of the REMBOW seat frame across the positions of the bolts, and the upper frame 32 of the REMBOW pad 30 can be fixed on the rods inserted in the respective attachment holes of the load cell sensors.

In another embodiment of the invention, the weighing unit 40 in FIG. 2 may comprise at least one weight sensor which is fixed on the upper surface of a lower frame 34 of the REMBOW pad 30. The weight of the occupant seated on the cushion 38 of the REMBOW pad 30 is applied then to the upper surface of a lower frame 34 through at least one weight sensor that converts the weight of the occupant sitting on a cushion 38 into an electric signal 31 (the weight signal indicative of the weight of the occupant).

In a frame of using the KEF technology, the weighing procedure can be described as follows. According to an embodiment of the present invention, when an occupant is not in the car seat yet, a voltage supply (not shown in FIG. 2) of the weighing unit 40 can be activated, for example, when the car door is opened, and the weighing unit 40 is automatically calibrated by itself. When the occupant sits down on the car seat, a beep can invite the occupant to fasten his/her seat belt. Before the seat belt is fastened, the occupant can be instructed to measure his/her weight by using the KEF technology. Some embodiments, described herein, disclose weight measurements performed with or without the seat belt being fastened, where the WEBEL method described above can be used for eliminating a small error for the weight measurement when the seat belt is fastened.

Furthermore, the occupant can initiate sending a starting signal 41 (which can be sent through a wired connection as shown in FIG. 2, or wirelessly through the communication device 48) to the controller/processor 44 to start recording weight measurements by finger pressing in the horizontal direction a switch/button of a weighing moderator/kemoder 50 (it is shown as element 210 in FIG. 1). The kemoder 50 can be located on a steering wheel, on a dashboard or in another place of the substantially vertical part of the vehicle above the waist of the occupant near his/her hand. As further described herein, the occupant can simultaneously easily and conveniently lift his/her feet from the floor due to an assisting force from a hand/finger pressing the switch/button of the weighing moderator/kemoder 50. After the weight measurement is completed during a short time interval, the occupant can fasten the seat belt whose switch can send a signal 37 to the controller/processor 44 to suppress the signal 41 sent from the weighing moderator 50 to the controller/processor 44.

According to a further embodiment, after the weighing units 40 is calibrated, the weight signal 31 can be provided to an electronic processing module 42 for a further processing. The module 42 can comprise a pre-amplifier, an amplifier, an analog-to-digital converter (ADC), normalizing unit and/or the like, which are known in the art, to provide a processed weight signal (e.g., a digital electric signal in a binary code) 33. After the controller/processor 44 receives the starting signal 41 from the weighing moderator 50, it will start to receive the processed weight signal 33 from the electronic processing module 42. The controller/processor 44 can provide, after a predefined processing using a memory 46 (storing weight measurement related applications), measured weight signals such as a signal 43a (through a wired connection) or a signal 43b (wireless through a communication device 48), and/or a further signal 45 (through the communication wireless device 48) to corresponding modules in the vehicle and outside the vehicle.

According to various embodiments described herein, the signal 43a or 43b can be provided to a vehicle electronic computing unit (ECU) 56 and comprise the measured weight signal indicative of the measured weight of the occupant of the vehicle (occupants weight with the clothes) for resolving safety issues associated with using an air bag. As described herein, determination of the measured weight of the occupant can be performed/adjusted by the controller/processor 44 using the WEBEL method, if the weight measurement of the occupant was performed with the seat belt being fastened. Moreover, the ECU unit 56 (which may comprise or be complimentary to a supplemental restraint system, SRS) can adjust a force of the air bag in action based on the measured weight of the occupant provided in the signal 43a or 43b, and using further sensor signals 47 from a module 54, indicating a strength of collision, indicating whether the seat belt being on/off, as well as a signal 35 (indicating a position of the occupant on the corresponding REMBOW pad) from the positioning sensors 36 located in the upper frame 32 of the REMBOW pad 30, as shown in FIG. 2.

Also, the signal 43a or 43b can be directed to a health indication and preventive system in the vehicle through the module 56 to perform various health related functions (such as obesity prevention program and the like) as described in detail in priority documents of the present invention, namely pending U.S. patent application Ser. No. 15/430,219 filed on Feb. 10, 2017 and U.S. Pat. No. 9,566,877 issued on Feb. 14, 2017. It is further noted that the signal 43a or 43b can provide the health-related signals (with an estimated weight of clothes being subtracted) of the occupants to the health indication and preventive system in the vehicle through the module 56. As stated herein, the controller/processor 44 can estimate a clothes weight of the occupant based at least on one or more of a geographical location of the vehicle, atmospheric temperature and/or a current date.

In addition, according to an embodiment described herein, the controller/processor 44 can provide, using a signal 45, the health-related weight and/or the measured weight of the occupant to the health indication and preventive system outside of the vehicle, e.g., to outside devices/systems 60 such as a personal computer (PC), a tablet, a smartphone a fitness terminal and the like to handle/manage, e.g., a pre-fitness program, a fitness program, an obesity prevention program, a kidney disease prevention program and the like.

Yet, in another embodiment, the signal 43a or 43b can comprise a warning signal that the measured weight of the occupant exceeds the predefined weighting range of the weighing unit 40 with an advise/request to substitute for an appropriate RENBOW pad with a larger weighing capacity is necessary.

According to a further embodiment, the controller/processor 44 can provide an ignition disabling signal 53 (through a wired connection, or wirelessly through the communication device 48) to an ignition system 52 of the vehicle, when the measured weight of a driver/occupant is in a predetermined range. Thus, the controller/processor 44 of the REMBOW pad 30 can be configured to disable an ignition system 52 of the vehicle using the signal 53 as described herein, e.g., for protecting a small child trying to drive a vehicle.

The controller/processor 44, can be a controller, microcontroller, a processor or a microprocessor or an equivalent processing device capable of executing commands of computer readable data or program for executing a control algorithm that controls the operation of the REMBOW pad 30 in order to perform the prescribed functions and desired processing, the controller 44 may include, but not be limited to, processor(s), computer(s), operation memory, storage, register(s), timing, interrupt(s), communication interfaces, and input/output signal interfaces, as well as combinations comprising at least one of the foregoing. For example, the controller may include input signal filtering to enable accurate sampling and conversion or acquisitions of such signals from communications interfaces. As described above, exemplary embodiments of the present invention can be implemented through computer-implemented processes and apparatuses for practicing those processes. A similar description can be applied to the ECU 56. Various embodiments of the controller/processor 44 or ECU 56 can include but are not limited to: general purpose computers, special purpose computers, microprocessors, microcontrollers, digital signal processors (DSPs), multi-core processors, embedded, and/or System on Chip (SoC) devices. According to further embodiments, the controller/processor 44 can perform some functionalities of the ECU 56, and vice versa, the ECU 56 can perform some functionalities of the controller/processor 44. Moreover, the controller/processor 44 can be combined with the ECU 56.

The memory (or at least one memory) 46 can be an operational memory of the controller/processor 44 or it can be a separate additional memory or multiple additional memories, depending on implementation needs. Various embodiments for the memory 46 (e.g., computer readable memory) may include any data storage technology type which is suitable to the local technical environment, including but not limited to: semiconductor based memory devices, magnetic memory devices and systems, optical memory devices and systems, fixed memory, removable memory, disc memory, flash memory, DRAM, SRAM, EEPROM and the like.

Any of weight measurement related applications can be stored in the memory 46, but in general it may be implemented as software, firmware and/or a hardware module, or a combination thereof. In particular, in the case of software or firmware, one embodiment may be implemented using a software related product such as a computer readable memory (e.g., non-transitory computer readable memory), computer readable medium or a computer readable storage structure comprising computer readable instructions (e.g., program instructions) using a computer program code (i.e., the software or firmware) thereon to be executed by a computer processor.

Figure 3:
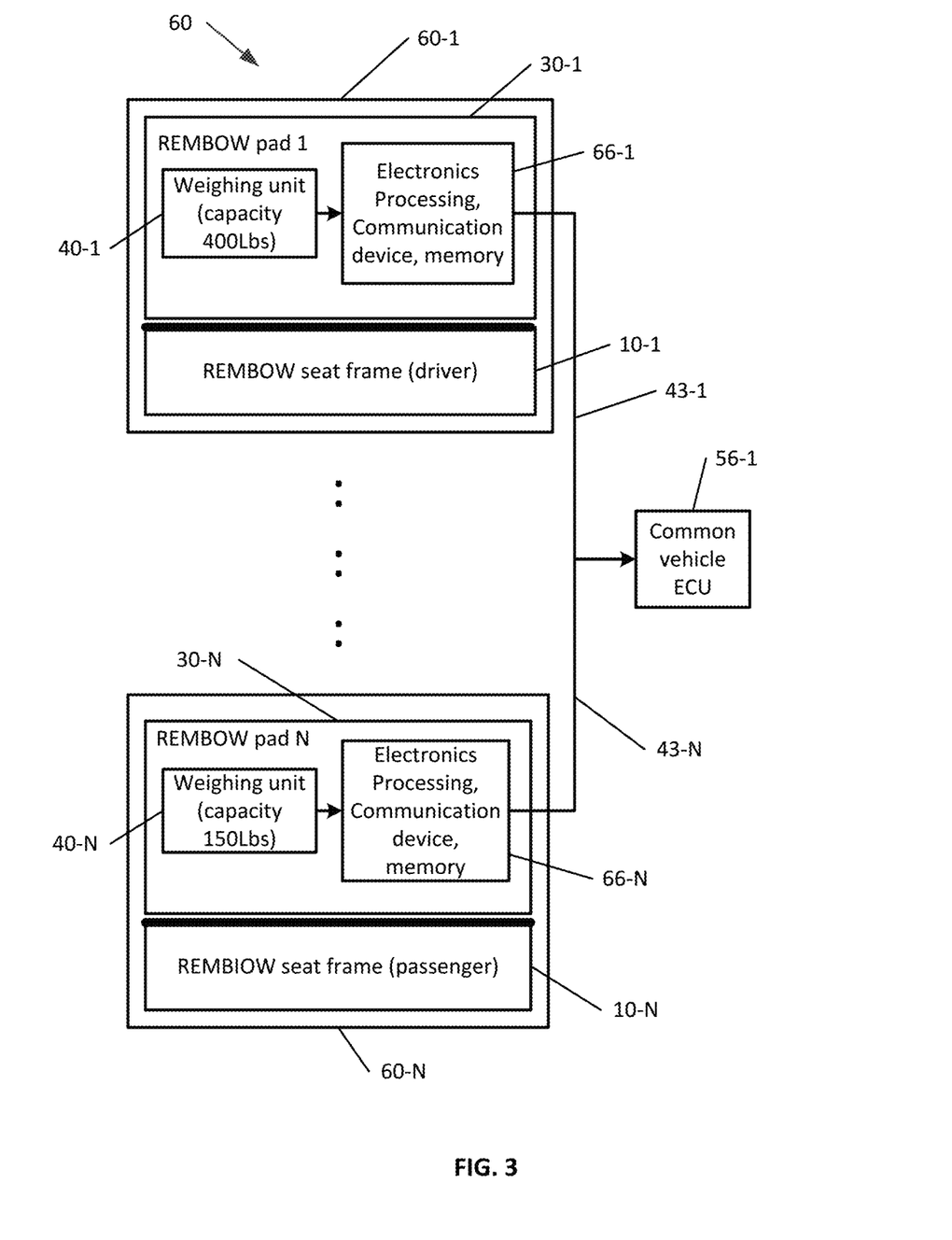
FIG. 3 is a non-limiting block-diagram of a REMBOW system in a vehicle comprising multiple REMBOW pads, according to an embodiment of the present invention.
Figure 4:
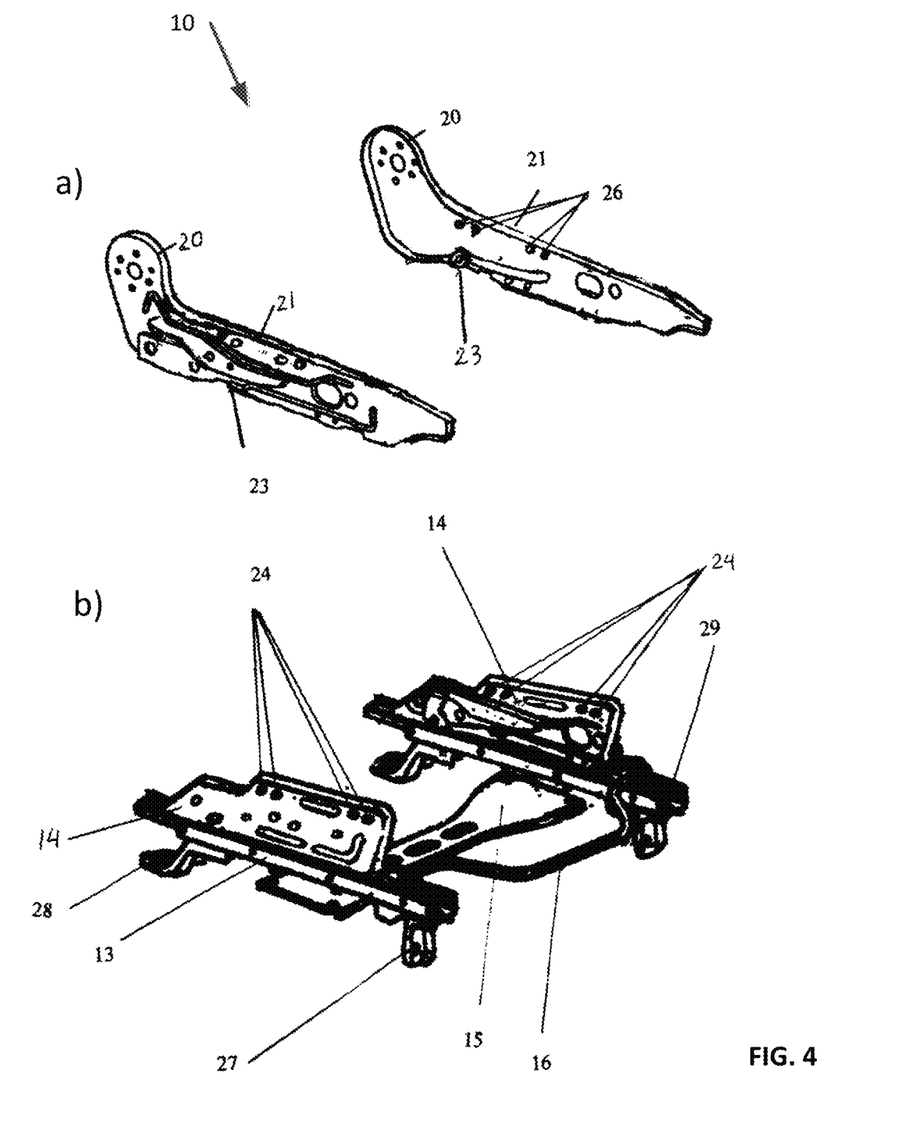
FIGS. 4a and 4b are views of different parts of a simplified structure of a seat frame (or a RAMBOW seat frame), which can be used for practicing various embodiments of the invention.
Figure 5:
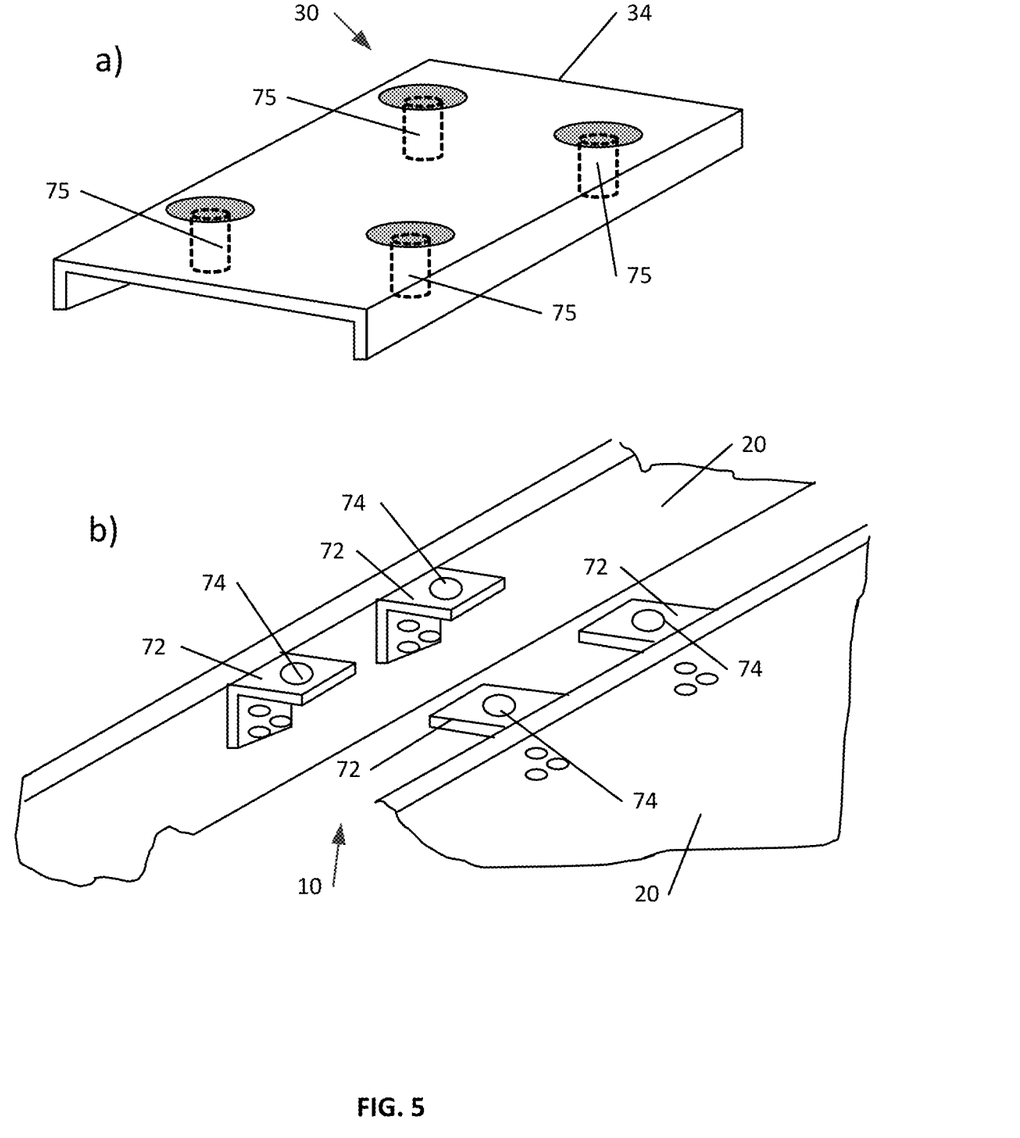
FIGS. 5a and 5b are views of two parts of a simplified structure for a detachable connection of a lower frame of a RAMBOW pad with a RAMBOW seat frame according to an embodiment of the present invention.

FIG. 3 shows a non-limiting block-diagram of a REMBOW system 60 comprising multiple (N) REMBOW pads 30-1, . . . , 30-N (discussed in detail in reference to FIG. 2) mounted on corresponding REMBOW seat frames 10-1, . . . , 10-N (where N being a finite integer, e.g., four, like for a family of four people) having different capacities of weighing units 40-1, . . . 40-N, each being similar to the weighing unit 40 in FIG. 2, for a driver and passengers on the front and for further/back seats 60-1 . . . . , 60-N of a car/vehicle, according to an embodiment of the present invention. The capacity of the weighing unit 40-1 is 400 pounds, and the capacity of the weighing unit 40-N is 150 pounds (e.g., for a lighter passenger, such as a teenager). Each REMBOW pad 30-1, . . . , or 30-N has a corresponding module 66-1, . . . , 66-N combining electronic, processing, communication and memory functions. In other words, each of the modules 66-1, . . . , 66-N is equivalent to a combination of modules 42, 44, 46 and 48 shown and discussed in reference to FIG. 2.

Measured weight signals 43-1, . . . , 43-N (each such a signal being equivalent to the signals 43a or 43b in FIG. 2) are provided to a common vehicle electronic computing unit (ECU) 56-1, which is similar to the vehicle ECU 56 of FIG. 2, but the common vehicle ECU 56-1 performs functionalities of the vehicle ECU 56 (which is set up for one REMBOW pad 30) for N REMBOW pads 30-1, . . . , 30-N, i.e., performing air bag control and/or health related functionalities, as described herein.

FIGS. 4a and 4b show a non-limiting example of a simplified structure of a seat frame (or a RAMBOW seat frame) 10, also shown as seat frames 10-1, . . . , 10-N in FIG. 3, which can be used for practicing various embodiments of the invention. As shown in FIG. 4b, according to one embodiment, the REMBOW seat frame 10 can comprise a left and right pair of lower rails 13 fixed on the floor of the vehicle, a left and right pair of upper sliding rails 14 engaged with the lower rails 13 so as to be capable of sliding on the respective lower rails 13 in a rear and front direction with respect to the lower rails 13. A lower bracket 15 is fixed to lower surfaces of the lower rails 13 and bridged between the left and right lower rails 13. A lock mechanism 16 locks the upper rails 14 to the lower rails 13 and releases the locking brackets 27 attached onto front end portions of the lower surfaces of the respective lower rails 13, and brackets 28 being attached onto rear end portions of the lower surfaces of the respective lower rails 13. The brackets 27 and brackets 28 are attached to the vehicle floor, to provide the lower rails 13 to be fixed to the vehicle floor. A slide adjuster 29 for adjusting a back-and-forth position of the vehicle seat is attached onto the floor and includes lower rails 13 and upper rails 14. A backrest frame can be located at a rear end of the side frame 20 (not shown in FIGS. 4a and 4b), which is capable of rising and falling by a reclining mechanism for supporting back cushion of a seat.

As further shown in FIGS. 4a and 4b, the REMBOW seat frame 10 can consist of two side frames 20 that are fixed by bolts and brackets through the holes 24 on the upper surfaces of the left and right upper rails 14. The upper portions 21 of the side frames 20 are horizontal. On each of these upper portions 21, the two brackets 26 are located by which the lower frame 34 of the REMBOW pad 30 (shown in FIG. 2) can be detachably connected, e.g., by clips, cylindrical or tapered pins, bars and the like directly to the side frames 20 and thus to the upper surfaces of the left and right upper rails 14.

In another embodiment, the side frames 20 can be covered with a rectangular REMBOW seat pan frame (not shown in FIGS. 4a and 4b), and the side frames 20 and the seat pan frame can be fixed to each other. The upper portion of the REMBOW seat pan frame can have clips, pins, bars and the like for mechanical attachment of the REMBOW pad 30.

In another embodiment of the invention, the surface of both the seat pan frame (if used) or side frames 20 of the REMBOW seat frame 10 and the lower frame 34 of the REMBOW pad 30 can have bulges and concavities to improve the stiffness. The location of a bulge on one of them can exactly match the concavity on the other that can provide secure and detachable mounting of the REMBOW pad 30 on the REMBOW seat frame 10.

FIGS. 5a and 5b demonstrate a non-limiting example of a simplified structure for a detachable connection of the lower frame 34 of the RAMBOW pad 30 shown in FIG. 5a with a seat frame (or a RAMBOW seat frame) 10 shown in FIG. 5b (also shown as seat frames 10-1, . . . , 10-N in FIG. 3) which can be used for practicing various embodiments of the invention. The lower frame 34 of the REMBOW pad 30 can provide secure detachable mounting of the RENBOW pad 30 on an upper surface of the side frames 20 of the REMBOW seat frame 10 using pins 75 having a cylindrical shape. The pins 75 can be connected to the lower frame 34 of the REMBOW pad 30 by welding and can be mounted on the upper surface of the side frames 20 of the RAMBOW seat frame 10 using corresponding holes 74 in four brackets 72. Various clips, pins, bars and the like described herein can be used to secure the attachment.

Figure 6:
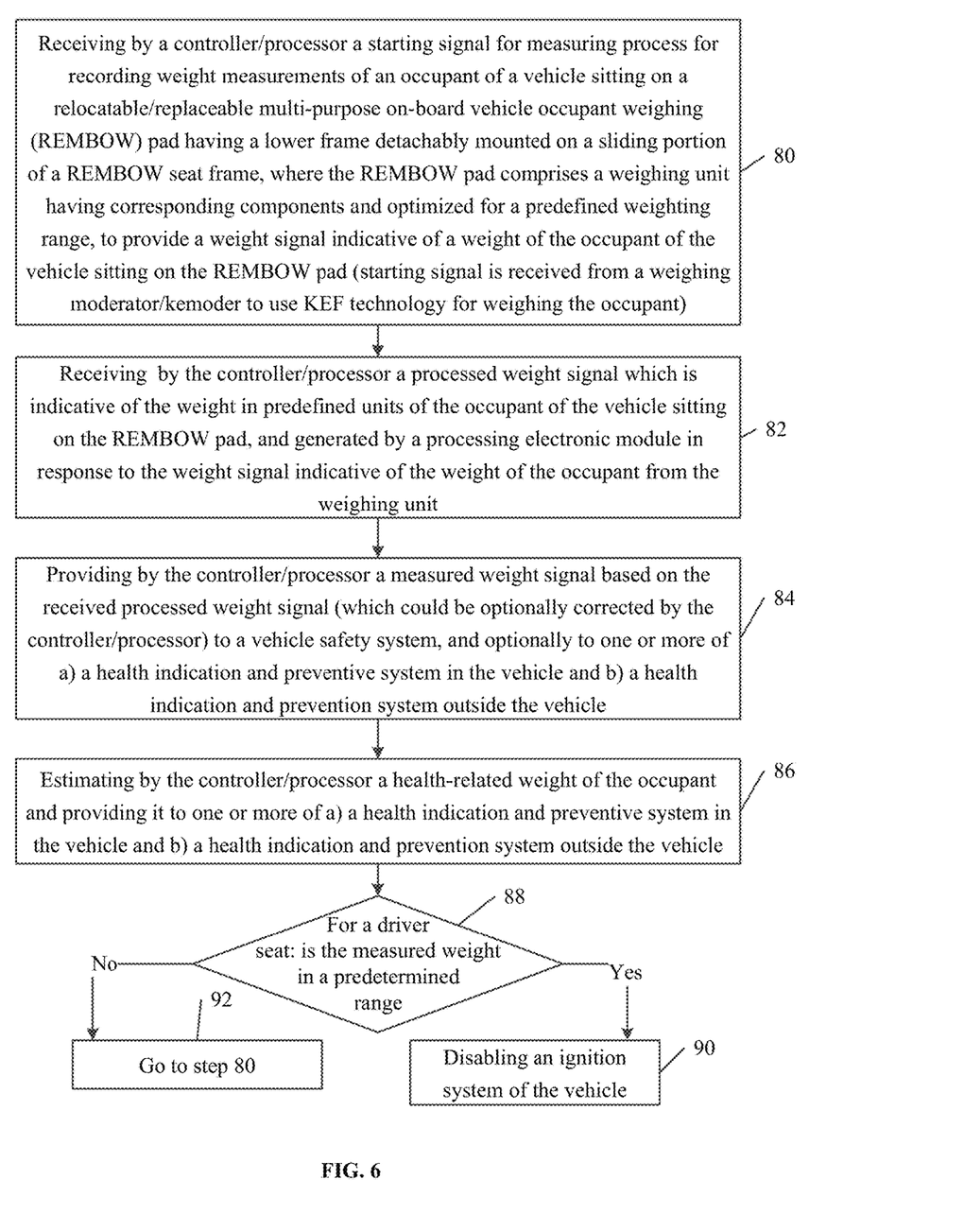
FIG. 6 is an exemplary flowchart for implementation of various embodiments of the invention.

FIG. 6 is an exemplary flowchart for implementation of embodiments, disclosed herein. It is noted that the order of steps shown in FIG. 6 is not required, so in principle, the various steps may be performed out of the illustrated order. Also certain steps may be skipped, different steps may be added or substituted, or selected steps or groups of steps may be performed in a separate application, following the embodiments described herein.

In a method according to this exemplary embodiment disclosed in reference to FIGS. 1-5, as shown in FIG. 6, in a first step 80, a computer/controller of a REMBOW pad, described herein, receives a starting signal for measuring process for recording weight measurements of an occupant of a vehicle sitting on a relocatable/replaceable multi-purpose on-board vehicle occupant weighing (REMBOW) pad having a lower frame detachably mounted on a sliding portion of a REMBOW seat frame, where the REMBOW pad can comprise a weighing unit having corresponding components and optimized for a predefined weighting range, to provide a weight signal indicative of a weight of the occupant of the vehicle sitting on the REMBOW pad (the starting signal is received from a weighing moderator/kemoder to use KEF technology for weighing the occupant).

In a next step 82, the computer/controller, in response to the starting signal, starts to receive a processed weight signal which is indicative of the weight in predefined units of the occupant of the vehicle sitting on the REMBOW pad and generated by a processing electronic module in response to the weight signal indicative of the weight of the occupant from the weighing unit.

In a next step 84, the computer/controller provides a measured weight signal based on the received processed weight signal (which could be optionally corrected by the controller/processor) to a vehicle safety system, and optionally to one or more of a) a health indication and preventive system in the vehicle and b) a health indication and prevention system outside the vehicle.

In a next step 86, the computer/controller estimates (optionally) a health-related weight of the occupant and providing it to one or more of a) a health indication and preventive system in the vehicle and b) a health indication and prevention system outside the vehicle.

In a next step 88, the computer/controller determines for a driver seat, whether the measured weight of a driver is in a predetermined range. If it is determined that the measured weight is in the predetermined range, the computer/controller disables an ignition system in the vehicle (e.g., to avoid a child driving). If, on the other hand, if it is determined that the measured weight is not in the predetermined range, the process goes back to step 80.

Unless defined otherwise, technical and scientific terms used herein have the same meaning as is commonly understood by one having ordinary skill in the art to which this disclosure belongs. The terms "first", "second", and the like, as used herein, do not denote any order, quantity, or importance, but rather are employed to distinguish one element from another. Also, the terms "a" and "an" do not denote a limitation of quantity, but rather denote the presence of at least one of the referenced items. The use of "including," "comprising" or "having" and variations thereof herein are meant to encompass the items listed thereafter and equivalents thereof, as well as additional items. The terms "connected" and "coupled" are not restricted to physical or mechanical connections or couplings, and can include electrical and optical connections or couplings, whether direct or indirect.

Furthermore, the skilled artisan will recognize the interchangeability of various features from different embodiments. The various features described, as well as other known equivalents for each feature, can be mixed and matched by one of ordinary skill in this art, to construct additional systems and techniques in accordance with principles of this disclosure.

In describing alternate embodiments of the apparatus claimed, specific terminology is employed for the sake of clarity. The invention, however, is not intended to be limited to the specific terminology so selected. Thus, it is to be understood that each specific element includes all technical equivalents that operate in a similar manner to accomplish similar functions.

It is to be understood that the foregoing description is intended to illustrate and not to limit the scope of the invention, which is defined by the scope of the appended claims. Other embodiments are within the scope of the following claims.

It is noted that various non-limiting embodiments described and claimed herein may be used separately, combined or selectively combined for specific applications. Further, some of the various features of the above non-limiting embodiments may be used to advantage, without the corresponding use of other described features. The foregoing description should therefore be considered as merely illustrative of the principles, teachings and exemplary embodiments of this invention, and not in limitation thereof.

What is claimed is:

1. A relocatable/replaceable multi-purpose on-board vehicle occupant weighing (REMBOW) pad for occupant weighing in a vehicle, the REMBOW pad comprising:
   a lower frame detachably mounted manually without tools on a sliding portion of a REMBOW seat frame;
   a weighing unit, attached to said lower frame, having corresponding components and optimized for a predefined weighting range, configured to provide a weight signal indicative of a weight of an occupant of the vehicle sitting on the REMBOW pad for generating a measured weight signal indicative of a measured weight of the occupant in order to secure a safe use of a corresponding air bag; and
   an upper frame comprising a seat cushion to cover parts of the REMBOW pad.

2. The REMBOW pad of claim 1, wherein the occupant weighing is performed using a kemoder elimination of a separate occupant's feet weighing (KEF) technology, where the kemoder is a key element for moderating (a weighing moderator) of accuracy and convenience of weighing and for generating a starting signal for measuring process.

3. The REMBOW pad of claim 1, further comprising a transceiver for providing communications, using wireless or wired connection, between the REMBOW pad and components/devices outside of the REMBOW pad in the vehicle or outside the vehicle.

4. The REMBOW pad of claim 1, wherein the lower frame is detachably mounted on side frames that are fixed on sliding rails of the REMBOW seat frame.

5. The REMBOW pad of claim 1, wherein the weighing unit is located in the lower frame.

6. The REMBOW pad of claim 1, wherein the vehicle is a self-driving car.

7. The REMBOW pad of claim 1, further comprising a controller/processor with a memory, for managing and coordinating performance of the weighing unit.

8. The REMBOW pad of claim 7, wherein the controller/processor is configured to identify the occupant of the vehicle and a corresponding record, using a fingerprint identifier.

9. The REMBOW pad of claim 7, wherein the controller/processor is configured to start recording weight measurements performed by the weighing unit in response to a corresponding starting signal for measuring process from a kemoder, where the kemoder is a weighing moderator and a key element for moderating of accuracy and convenience of weighing and for generating the starting signal for measuring process.

10. The REMBOW pad of claim 9, wherein the weighing moderator comprises an audio command module configured to provide the corresponding starting signal activated by a voice of the occupant of the vehicle.

11. The REMBOW pad of claim 9, further comprising a processing electronic module, for providing to the controller/processor, when the starting signal is received by the controller/processor, the processed weight signal which is indicative of the weight in predefined units of the occupant of the vehicle sitting on the REMBOW pad, and generated in response to the weight signal indicative of the weight of the occupant from the weighing unit, so that the controller/processor is further configured, in response to the processed weight signal, to provide the measured weight signal indicative of a measured weight of the occupant to any of a) a vehicle safety system to adjust a force of the corresponding air bag in action, b) a health indication and preventive system in the vehicle and c) a health indication and prevention system outside the vehicle.

12. The REMBOW pad of claim 11, wherein the controller/processor is configured to provide a warning signal that the measured weight of the occupant exceeds the predefined weighting range of the weighing unit and that it is necessary to substitute for a further RENBOW pad with a larger weighing capacity, so that the REMBOW pad is replaced manually without tools to the further REMBOW pad with the larger weighing capacity.

13. The REMBOW pad of claim 11, wherein the REMBOW pad is detachably mounted on the REMBOW seat frame of a driver of the vehicle, so that when the measured weight is in a predetermined range, the REMBOW pad is configured to disable an ignition system of the vehicle.

14. The REMBOW pad of claim 10, wherein the controller/processor is configured to estimate a clothes weight of the occupant based at least on a geographical location of the vehicle, atmospheric temperature and a current date, and to subtract the estimated clothes weight from the measured weight of the occupant to determine an approximate true weight of the occupant.

15. The REMBOW pad of claim 14, wherein the REMBOW pad is configured to provide the approximate true weight of the occupant to one or more of a) a health indication and preventive system in the vehicle and b) a health indication and prevention system outside the vehicle.

16. The REMBOW pad of claim 1, wherein the weighing unit comprises strain gages that are fixed on the lower frame of the REMBOW pad, the upper frame of the REMBOW pad is fixed on the strain gages.

17. The REMBOW pad of claim 1, wherein the weight signal is generated without a seat belt being fastened, so that the measured weight signal indicative of the measured weight of the occupant directly corresponds to the weight signal.

18. The REMBOW pad of claim 1, wherein the weight signal is generated with a seat belt being fastened, so that the measured weight signal indicative of the measured weight of the occupant without the seat belt being fastened is extrapolated using a statistically derived coefficient between weight measurements with or without seat belt being fastened, using a Weight Error from the Belt Elimination (WEBEL) method.

19. A non-transitory computer readable storage medium tangibly storing computer program instructions capable of being executed by a computer processor, the computer program instructions defining code for:
   receiving a starting signal for recording weigh measurements of an occupant in a vehicle sitting on a relocatable/replaceable multi-purpose on-board vehicle occupant weighing (REMBOW) pad having a lower frame detachably mounted manually without tools on a sliding portion of a REMBOW seat frame, where the REMBOW pad comprises a weighing unit, attached to said lower frame, having corresponding components and optimized for a predefined weighting range, and configured to provide a weight signal indicative of a weight of an occupant of the vehicle sitting on the REMBOW pad
   receiving, in response to the starting signal, a processed weight signal, in predefined units, of the occupant of the vehicle sitting on the REMBOW pad from a processing electronic module of the REMBOW pad which is responsive to the weight signal indicative of the weight of the occupant from the at least one weighing unit;

providing, based on the received the processed weight signal, a measured weight signal indicative of a measured weight of the occupant of the vehicle to a vehicle safety system in order to secure a safe use of a corresponding air bag.

20. A relocatable multi-purpose on-board vehicle occupant weighing (REMBOW) system comprising:

a vehicular seat frame comprising a sliding portion, a relocatable/replaceable multi-purpose on-board vehicle occupant weighing (REMBOW) pad for occupant weighing in a vehicle, the REMBOW pad comprising:

a lower frame detachably mounted manually without tools on the sliding portion of a REMBOW seat frame; and a weighing unit, attached to said lower frame, having corresponding components and optimized for a predefined weighting range, configured to provide a signal indicative of a weight of an occupant of the vehicle sitting on the REMBOW pad for generating a measured weight signal indicative of a measured weight of the occupant of the vehicle; and an upper frame comprising a seat cushion to cover parts of the REMBOW pad; and a vehicular control system configured to secure a safe use of a corresponding air bag based on the measured weight signal.

\* \* \* \* \*